(12) United States Patent
Lazarev et al.

(10) Patent No.: US 6,281,503 B1
(45) Date of Patent: Aug. 28, 2001

(54) NON-INVASIVE COMPOSITION ANALYSIS

(75) Inventors: Pavel Lazarev, Belmont; Mikhail Paukshto, San Mateo, both of CA (US)

(73) Assignee: Quanta Vision, Inc., San Mateo, CA (US)

( * ) Notice: Subject to any disclaimer, the term of this patent is extended or adjusted under 35 U.S.C. 154(b) by 0 days.

(21) Appl. No.: 09/286,170

(22) Filed: Apr. 5, 1999

Related U.S. Application Data

(63) Continuation-in-part of application No. 09/073,720, filed on May 16, 1998, now Pat. No. 6,175,117.

(51) Int. Cl.$^7$ .................................................. G01N 23/20
(52) U.S. Cl. ............................... 250/363.01; 250/370.09
(58) Field of Search ..................... 250/363.01, 363.09, 250/370.08, 370.09, 390.04, 395; 378/37; 600/407; 702/28

(56) References Cited

U.S. PATENT DOCUMENTS

| | | | |
|---|---|---|---|
| 3,973,126 | 8/1976 | Redington et al. | 250/444 |
| 4,365,303 | 12/1982 | Hannah et al. | 364/498 |
| 4,515,165 | 5/1985 | Carroll | 128/664 |
| 4,549,307 | 10/1985 | Macovski | 378/145 |
| 4,651,002 | 3/1987 | Anno | 250/336.1 |
| 4,751,722 | 6/1988 | Harding et al. | 378/6 |
| 4,754,469 | 6/1988 | Harding et al. | 378/88 |
| 4,807,637 | 2/1989 | Bjorkholm | 128/664 |
| 4,887,285 | 12/1989 | Harding et al. | 378/88 |
| 4,962,515 | 10/1990 | Kopans | 378/37 |
| 4,969,174 | 11/1990 | Scheid et al. | 378/146 |
| 5,150,395 | 9/1992 | Kosanetzky et al. | 378/86 |
| 5,212,719 | 5/1993 | Virta et al. | 378/155 |
| 5,386,447 | 1/1995 | Siczek | 378/37 |
| 5,491,738 | 2/1996 | Blake et al. | 378/71 |
| 5,604,783 | 2/1997 | Charpak | 378/146 |
| 5,684,851 | 11/1997 | Kurbatov et al. | 378/87 |
| 5,717,733 | 2/1998 | Kurbatov et al. | 378/71 |
| 5,741,707 | 4/1998 | Herron et al. | 436/25 |
| 5,748,509 | 5/1998 | Fewster et al. | 364/578 |

FOREIGN PATENT DOCUMENTS

| | | | |
|---|---|---|---|
| 0 402 082 A1 | 12/1990 | (EP) | A61B/6/06 |
| 0 390 653 B1 | 6/1992 | (EP) | A61B/6/00 |
| 0 743 810 A1 | 11/1996 | (EP) | H05G/1/26 |
| 2 299 251 A | 9/1996 | (GB) | G01N/23/207 |
| 1402871 A1 | 11/1986 | (RU) | G01N/23/08 |
| 2012872 C1 | 5/1994 | (RU) | G01N/23/02 |
| WO 95/05725 | 2/1995 | (WO) | H05G/1/02 |
| WO 96/23209 | 8/1996 | (WO) | G01N/23/04 |

OTHER PUBLICATIONS

Zheleznaya, L. et al., "X–ray Diffraction Studies on Fine Structure of Mucus Glycoprotein", *Nanobiology*, vol. 1, pp. 107–115 (1992).

Harding, G. et al., "Elastic scatter computed tomography", *Phys. Med. Biol.*, vol. 30, No. 2 (1985), pp. 183–186.

Harding, G. et al., "A K edge filter technique for optimization of the coherent–to–Compton scatter ratio method", *Med. Phys.*, vol. 22, No. 12 Dec. 1995, pp. 2007–2014.

O. Glatter,*Modern Methods of Data Analysis in Small–Angle Scattering and Light Scattering, Modern Methods of Data Analysis in Small–Angle Scattering and Light Scattering*, H. Brumberger (ed.), 1995, Kluwer Academic Publishers, pp. 107–180.

*Primary Examiner*—Scott J. Sugarman
*Assistant Examiner*—Richard Hanig
(74) *Attorney, Agent, or Firm*—David J. Weitz; Wilson Sonsini Goodrich & Rosati

(57) ABSTRACT

A method for characterizing a test sample of biological tissue is disclosed. The method includes obtaining a radiation scattering pattern produced by the test sample of biological tissue and processing the radiation scattering pattern to determine a pair distance distribution function for the test sample. The method also includes comparing sample data derived from the pair distance distribution function with known data derived from known samples which each have one or more known characteristics.

28 Claims, 9 Drawing Sheets

NON-INVASIVE COMPOSITION ANALYSIS

CROSS-REFERENCE TO RELATED APPLICATIONS

This application is a Continuation-in-Part of U.S. application Ser. No. 09/073,720; filed May 16, 1998 now U.S. Pat. No. 6,175,117; entitled Tissue Analysis Apparatus and incorporated herein by reference in its entirety.

BACKGROUND OF THE INVENTION

1. Field of the Invention

The present invention relates to an apparatus and method for characterizing samples having periodic structures. More particularly, the present invention relates to a method and apparatus for processing structural functions of a tissue sample in order to characterize the tissue sample.

2. Description of Related Art

The ability to characterize biological tissues can be of great value in scientific research as well as in the diagnosis of diseases and other maladies. For instance, the ability to identify the type and quantity of cancerous tissues at various stages of a cancer's development can lead to selection of the correct therapy and can save the lives of many patients. However, the complexity of biological tissues has caused the characterization of biological tissues to be very challenging.

One technique for identifying and characterizing various tissues is to take an x-ray of the tissue. An x-ray is an image of the tissue which is formed by measuring how much each portion of the tissue absorbs x-ray radiation. Portions of the tissue with an increased absorption of x-rays generally show up as darker areas on the image while portions with a decreased absorption show up as lighter areas. However, different substances can have similar absorptions. Accordingly, the existence of the two substances can be overlooked and the tissue misdiagnosed.

When an x-ray indicates that cancerous tissues may exist a biopsy is frequently performed. The biopsy process includes inserting a needle into the tissue in order to remove a portion of the suspicious tissue. The tissue is sent to a lab so it can be identified. The biopsy procedure can be painful. Further, obtaining the results can be time consuming since they must be sent to a lab.

For these reasons, there is a need for an apparatus and method for distinguishing between the different tissues within a tissue sample. There is also a need for an apparatus and method which reduces the need for a biopsy and which reduce the time required to identify tissues which may be of interest.

SUMMARY OF THE INVENTION

The invention relates to a method for characterizing a test sample of biological tissue. The method includes obtaining at least a portion of a radiation scattering pattern produced by the test sample of biological tissue and processing the obtained radiation scattering pattern to determine a pair distance distribution function for the test sample. The method also includes comparing sample data derived from the pair distance distribution function with known data derived from known samples which each have one or more known characteristics. The comparison producing data about the character of the biological sample.

The invention also relates to a method for characterizing a biological sample. The method includes providing a plurality of relationships between the value of a characteristic and the value of a structural function at a particular point. The method also include identifying the value of a structural function developed from the biological sample at one or more points where the structural function is known to be sensitive to changes in the value of the characteristic and comparing the identified values with the provided relationships to determine a plurality of possible approximate values for the characteristic.

The invention also relates to a method for developing a normalized structural function for a biological sample. The method includes obtaining at least a portion of a structural function for the biological sample and identifying a value of the obtained portion at a point where the structural functions of a plurality of known samples each illustrate a common feature. The method also includes determining a ratio between the obtained structural function and the identified value over a range of the obtained structural function.

Another embodiment of the method for developing a normalized structural function includes concurrently determining at least a portion of a structural function for the biological sample and at least a portion of a structural function for a standard. The method also includes determining a ratio between at least a portion of the structural function obtained for the biological sample and at least a portion of the structural function obtained for the standard.

The invention also relates to a method for identifying points of a structural function which are sensitive to changes in the value of a characteristic. The method includes fitting a plurality of curves to data for known samples. The data for the known sample includes the value of the characteristic for each known sample and a value of a structural function for each known sample. The value of the structural function for each known sample is taken at a particular point along the structural function. As a result, each relationship is associated with a particular point along the structural function. The method also includes determining the mean deviation between each relationship and the data used to create each relationship and determining the variance of each relationship. The method further includes: identifying relationships with a relatively high ratio of variance to mean deviation; and characterizing the particular point along the structural function which is associated with the identified relationships as being a point which is sensitive to changes in the characteristic value.

The invention also relates to a computer readable medium which has stored thereon computer executable logic which, when executed by a processor, cause the processor to perform the acts of: obtaining at least a portion of a radiation scattering pattern produced by a test sample of biological tissue; processing the obtained radiation scattering pattern to determine a pair distance distribution function for the test sample; and comparing sample data derived from the pair distance distribution function with known data derived from known samples which each have one or more known characteristics.

DETAILED DESCRIPTION

Figure 1:
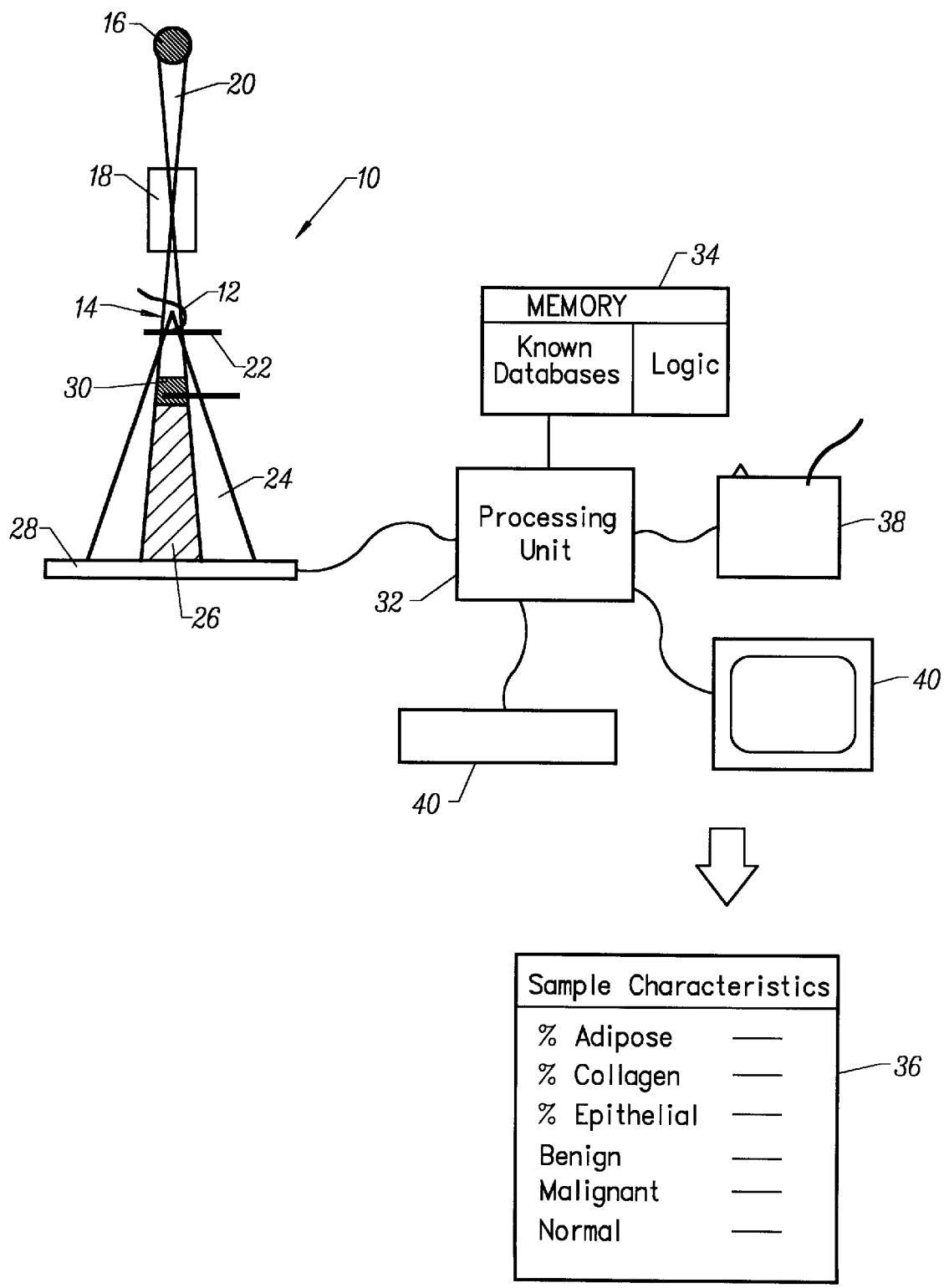
FIG. 1 illustrates a system for performing the methods of the present invention.

The present invention relates to a method and apparatus for characterizing a biological test sample. Characterization includes quantifying various characteristics of the sample. Suitable characteristics for quantization include, but are not limited to, the concentration of adipose, collagen or epithelial and/or the percent likelihood of the sample including tissues which are benign, normal or malignant and even more specific characterizations such as the percent likelihood that the sample includes a fibroadenoma. Suitable characteristics for determination also include qualitative characteristics. Example qualitative characteristics include, but are not limited to, normal, benign and malignant tissue and even more specific classifications such as whether the sample includes a fibroadenoma.

The methods and apparatus of the present invention stem from the applicant's recognition that the periodic nature of biological samples would cause those samples to have unique and useful structural functions. A structural function is a result of the structure and composition of a sample. Accordingly, samples with different structures and/or different compositions will have different structural functions. Examples of structural functions for use with the present invention include, but are not limited to, pair distance distribution functions and scattering-diffraction intensity angle distribution functions which are called scattering patterns below.

The structure of a biological sample can be a key element in correctly diagnosing the pathological condition of the sample. For instance, collagen is a highly abundant and periodic component of many biological tissues. The synthesis of collagen is part of the response to immunological aggression such as cancer inflammation, etc. As a result, the structure of collagen changes in response to the pathological condition of the tissue. This feature permits the structure of collagen to serve as an indicator of a tissue sample's pathological condition. Since a sample's structure can indicate the sample's pathological condition and since structural functions result from a sample's structure, the applicant has recognized that these functions are an ideal vehicle for diagnosing the pathological condition of biological samples.

The application of structural functions to biological samples provides several unique challenges when characterizing biological samples which are in their natural state, i.e., in vivo samples or in vitro samples which have not undergone extensive preparation or crystallization. For instance, two biological samples with the exact same composition can have a nearly infinite number of different structures. This characteristic can be illustrated by considering an in vivo sample of muscle tissue. The muscle tissue in its flexed state will have a different structural function than the same sample of muscle in its relaxed state. Additionally, biological samples can have a large number of compositions both in terms of the substances which make up the sample and the relative quantities of those substances. These characteristics of biological tissues increase the complexity which is required in order to obtain a successful characterization.

Another challenge presented by biological samples is the unusually large distance between the repeating structures within the sample. As indicated by Bragg's equation, this large distance causes the scattering angles associated with those repeating structures to be very small. The methods of the present invention can require identifying the intensity of radiation scattered at these very small angles. Identifying this intensity requires very precise equipment which has an accentuated sensitivity to day-to-day equipment variations such as variations in optical systems, electronics and radiation source. These variations can result from changes in light conditions, temperature and a variety of other factors which are difficult to control. The present invention provides systems methods and apparatuses which reduce the effects of these variations.

Figure 7:
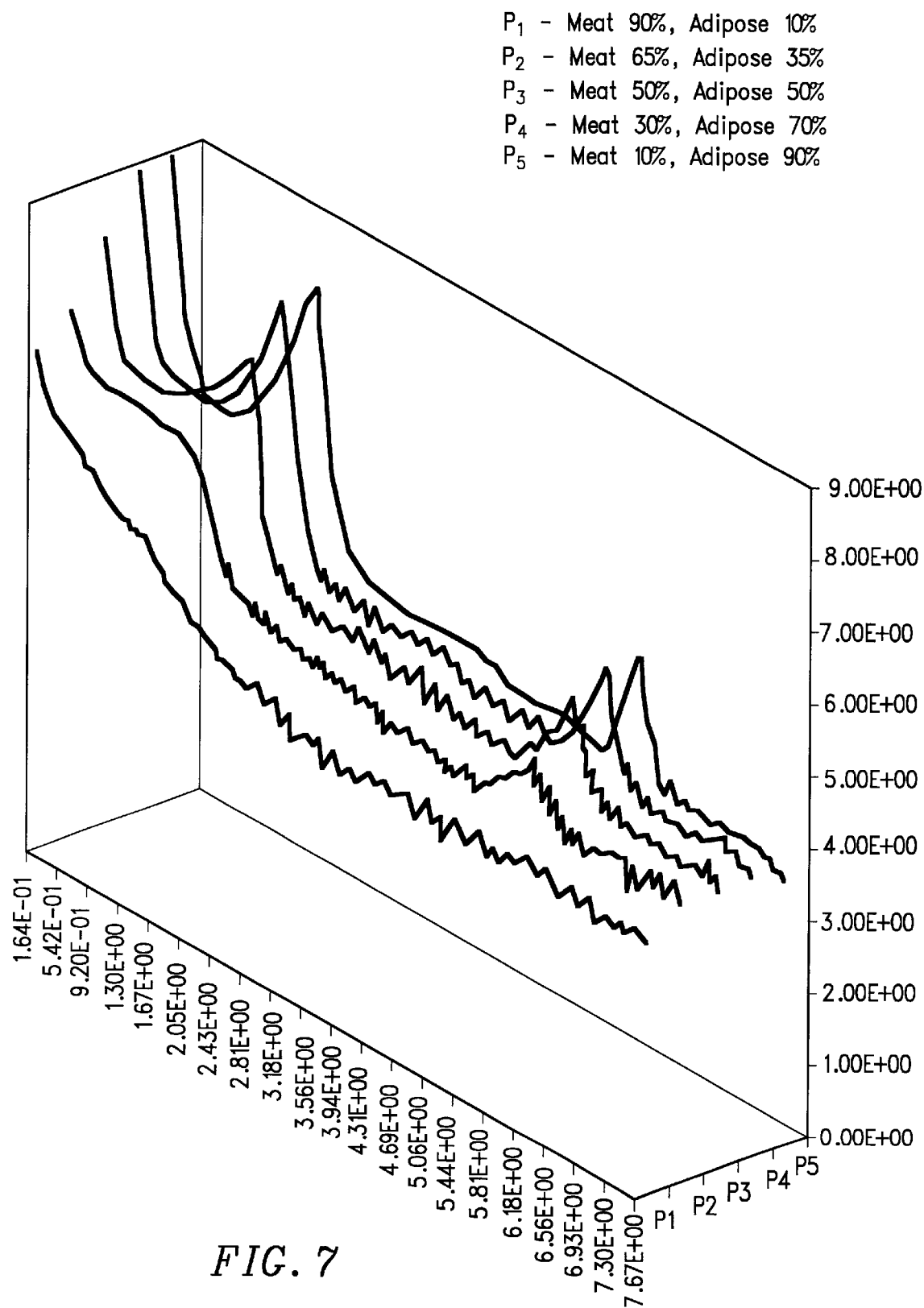
FIG. 7 illustrates a scattering pattern of several known samples.

As describe above, suitable structural functions for use with the present invention include scattering patterns and pair distance distribution functions. FIG. 7 illustrates the scattering patterns for samples composed of varying concentrations of adipose and meat. The scattering pattern is illustrated as a plot of intensity versus angle. The angle axis refers to the angle which radiation was scattered by the sample also called the scattering angle. The intensity axis refers to the intensity, or amount, of the radiation scattered at an angle on the angle axis. As a result, a scattering pattern or a portion of a scattering pattern can be determined by measuring the intensity of radiation scattered at different angles. In a computer or other processing unit, a scattering pattern can be stored as a mathematical formula or as a datastructure which associates an intensity of scattered radiation with a particular angle, with a range of angles or at a range of angles associated with a single specified angle.

Each component in a biological sample has a unique scattering pattern. Since scattering patterns of various components are known to be additive, the scattering pattern for the sample can be derived from the scattering pattern of each component making up the sample. Specifically, the scattering patterns for the components in a sample can be added in proportion to the percentage of the component in the sample to yield the scattering pattern of the sample. As a result, the scattering pattern for a sample is a function of the type and quantity of components in the sample. Accordingly, the scattering pattern for a sample reveals information about the type, quantity and structure of components in the sample and is an ideal vehicle for characterizing the sample.

Figure 8:
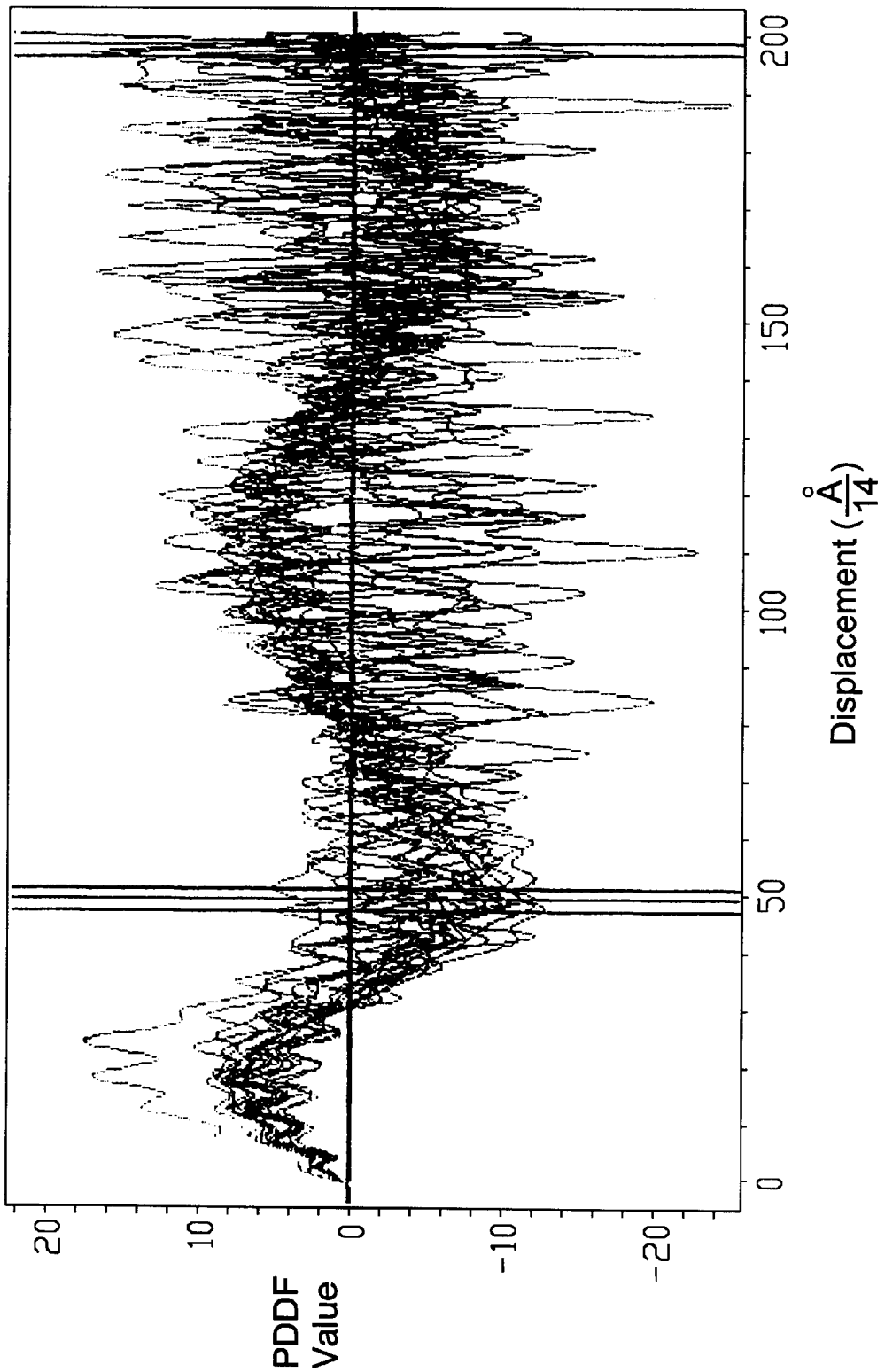
FIG. 8 illustrates the pair distance distribution function, PDDF, for fifty samples of normal breast tissue.

The pair distance distribution function, PDDF, is a function of the distance between typical points in the sample. Specifically, the value of the PDDF at a particular distance is proportional to the number of particles displaced by that distance within the sample. The PDDFs for fifty normal samples of breast tissue are shown in FIG. 8. The PDDF is known to be related to the scattering pattern by a Fourier transform. Specifically, the PDDF of the sample can be Fourier transformed to provide the scattering pattern of the sample and the scattering pattern can be inversely Fourier transformed to determine the PDDF.

The systems, methods and apparatuses of the present invention permit the structural functions to be normalized. This normalization permits comparison of different structural functions by reducing the effects of equipment variations. One method for normalization involves identification of a peak which appears at approximately the same distance in the PDDFs of all the biological samples developed with a given system. A normalized PDDF, NPDDF, can be produced by dividing a PDDF by the value of the PDDF at the common peak.

Another method for normalizing structural functions involves using the same equipment to concurrently determine the scattering pattern for a standard and the sample. The scattering pattern of the sample can then be divided by the scattering pattern of the standard to provide a normalized scattering pattern. Additionally, both scattering patterns can be converted to a PDDF and then the PDDF for the sample can be divided by the PDDF for the standard in order to develop an NPDDF.

Once an NPDDF is determined for a sample, a normalized scattering pattern can be determined by performing a Fourier transform on the NPDDF.

The normalized structural functions described above are used in a two phase process for characterizing a biological sample. The first phase includes data preparation and the second phase includes sample characterization. The data preparation phase is used to develop data for application in the sample characterization phase. For instance, various sensitive points are identified and stored for use in the sample characterization phase. The sensitive points are points along a structural function where the value of the structural function is sensitive to changes in the value of a characteristic which is to be studied in the sample characterization phase. These sensitive points are identified because they are the ideal points to study the relationship between the value of the particular characteristic and the value structural function at the sensitive point. Accordingly, the identification of these sensitive points provides a necessary reduction in the complexity of studying the structural functions of biological samples which is not necessary in non-biological samples.

Since the sensitive points define where a structural function is sensitive to changes in a particular characteristic, relationships between the value of the characteristic and the value of the structural function at each sensitive point are also determined in the data preparation phase. These relationships are stored for use with the sample characterization phase. Because the sensitive points and relationships are developed for a particular characteristic, the sensitive points and relationships are said to be associated with a particular characteristic. Additionally, each relationship is associated with a particular sensitive point since each relationship is developed using the value of the structural function at a sensitive point.

The data preparation phase works from a database of known samples. In the database, each known sample is associated with its characteristics and at least one structural function and/or normalized structural function. The known samples can optionally be classified according to their characteristics. For instance, the known samples can be classified as being normal, malignant or benign or can be classified as having a characteristic value above or below various threshold values. It is conceivable that a single unknown sample can fall into more than one class within the database.

The sensitive points and the relationships are determined by comparing the structural functions in the database against one another. During these comparisons the structural functions which are compared against one another are from the same classification. Accordingly, each sensitive point and relationship is associated with a particular class in addition to being associated with a particular characteristic as described above.

In the sample characterization phase, the scattering pattern for the sample is determined. The determined scattering pattern is then processed to determine a normalized structural function for the unknown sample. The value of the normalized structural function is determined at each of the sensitive points. The value of the structural function at each sensitive point is compared against the relationship associated with that sensitive point. This comparison yields a possible approximate characteristic value. The deviation among the possible approximate characteristic values is determined for the possible approximate characteristic values corresponding to each class of known samples. The set of possible approximate characteristic values having the lowest deviation is identified. The sample is characterized as having the average of the possible approximate characteristic values in the identified set and as belonging to the class of known samples with the lowest deviation. Accordingly, when the known samples are classified as normal, benign and malignant, the sample can be classified as normal, benign or malignant.

The sample characterization phase can exist independently from the data preparation phase. For instance, the sample characterization phase can be performed while knowing only the sensitive points and the sets of equations. Accordingly, numerous samples can be characterized without having to re-perform the data preparation phase.

FIG. 1 illustrates a system for performing a method of the present invention. The system includes a scattering pattern determination apparatus 10. The apparatus 10 includes a sample receiving volume 12 for receiving the sample 14. Suitable scattering pattern determination apparatuses 10 are described in the U.S. patent application Ser. No. 09/073,720, entitled Tissue Analysis Apparatus and filed on May 6, 1998 and hereby incorporated by reference. Although the illustrated sample 14 is a breast, the sample 14 can be another body part or an in vitro sample 14.

The apparatus 10 includes a radiation source 16 and a collimator 18 for forming radiation from the radiation source 16 into one or more beams 20 which are incident upon the sample 14. The sample receiving area can optionally include one or more surfaces 22 for encouraging correct positioning of the sample 14 within the one or more beams 20. As the beam 20 passes through the sample 14 a portion of the beam 20 is scattered 24 by the sample 14 while a portion of the beam is transmitted 26 through the sample 14 without being scattered. The apparatus 10 includes a detector 28 which receives at least a portion of the scattered beam 24. The apparatus 10 can optionally include a filter 30 which serves to screen the detector 28 from the transmitted portion of the beam 26.

The detector 28 can have a resolution which can distinguish photons which are scattered on the order of arc seconds. As a result, the apparatus 10 can measure the small angle scattering pattern of the sample 14. For instance, the scattering pattern can be determined for radiation scattered from as little as one arc seconds to one arc minute and larger. The ability to detect the small angle scattering pattern is important for biological substances. As discussed above, biological substances are known to have periodic structures. The distance between repeating structures is known to be large. Bragg's equation shows that this distance is inversely related to the scattering angle. Accordingly, biological tissues scatter radiation over small angles on the order of tens of arc seconds. As a result, the scattering patterns for use in with the present invention preferably extends from 0–42 degrees, more preferably from 0 to 2.1 degrees and most preferably from 0 to 15 arc minutes Additional scattering patterns extend up to 2 degrees, 1 degree, 10 arc minutes and 1 arc minute.

A processing unit 32 receives signals from the detector 28. processing unit 32 includes logic for discerning the scattering pattern of the sample from the signals received from the detector 28. Suitable processing units 32 include, but are not limited to a PC.

The processing unit 32 is also in communication with a memory 34 which includes a database where each of the known samples is associated with its known characteristics and one or more structural functions and/or normalized structural functions. The memory 34 also includes logic which is accessed by the processing unit 32. The logic can include logic for the data preparation phase and logic for the sample characterization phase. The data preparation logic processes the data associated with the known samples to determine the sensitive points and to determine the relationships between the value of the structural function at the sensitive points and the characteristic. The sample characterization logic includes logic for discerning a normalized structural function of the sample 14, identifying the value of the structural function at the sensitive points and comparing the determined values with the relationships determined in the data preparation phase.

Once the processing unit 32 characterizes the sample 14, the processing unit 32 can optionally produce a characterization report 36 which is printed out on a printer 38 or appears on a user interface 40 such as a monitor. Suitable characteristics for including in the characterization report 36 include, but are not limited to, the concentration of various components, the likelihood of the sample including various components. Characteristics such as concentrations can be expressed as molarity, volume percentage, mass percentage, etc. Other suitable characteristics for including in the report include whether the sample 14 is a normal tissue, a benign tissue or a malignant tissue.

Figure 2:
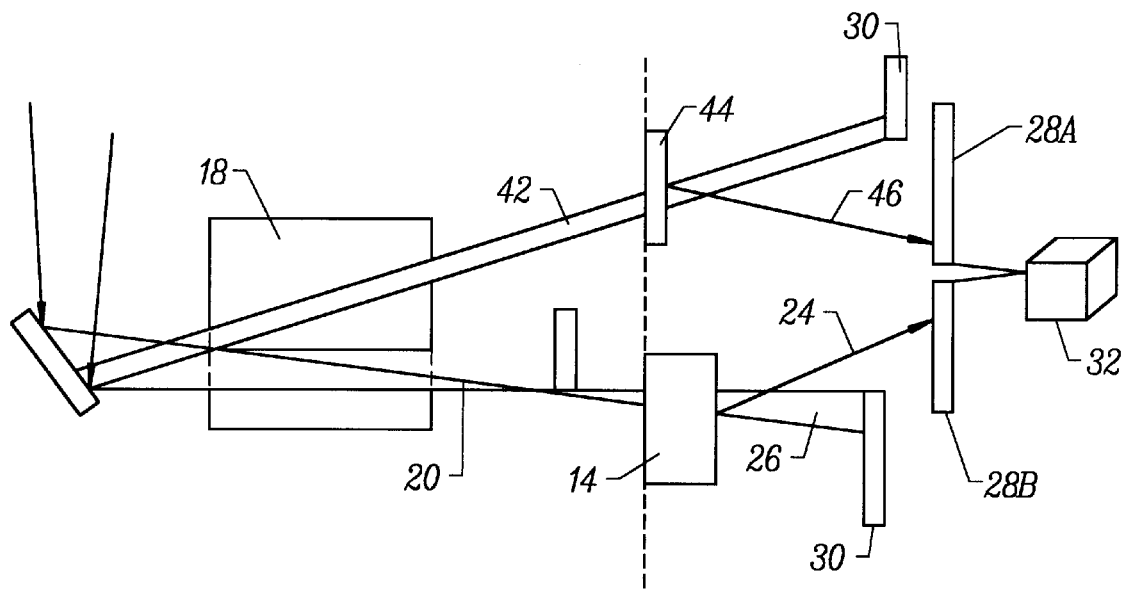
FIG. 2 illustrates an apparatus which includes a beam for identifying a structural function for a standard which is to be used during normalization.

FIG. 2 illustrates another embodiment of a scattering pattern determination apparatus 10. The collimator 18 forms radiation from a radiation source 16 into one or more beams 20 sample beams and into a standard beam 42. The standard beam 42 passes through a standard 44 and the scattered portion of the standard beam 46 is received at a standard detector 28A. The one or more sample beams 20 pass through the sample 14 to be characterized and the scattered portion of the one or more sample beams 24 is received at a sample detector 28B.

A processing unit 32 receives signals from the standard detector 28A and from the sample detector 28B. The processing unit 32 includes logic for processing these signals to discern at least a portion of the scattering pattern from the sample 14 and at least a portion of the scattering pattern from the standard 44. A ratio between the scattering pattern from the sample 14 and the scattering pattern from the standard is determined. For instance, the scattering pattern from the sample 14 can be divided by the scattering pattern from the standard 44 to provide a normalized scattering pattern. Because any systemic variations will be present in the scattering patterns from both the sample and the standard, this normalized scattering pattern will reduce any effects from variations in the equipment.

Although FIGS. 1 and 2 illustrate processing unit 32 based system for performing a method of the present invention, it is understood that the methods can be carried out manually or by some combination of automated and manual calculations.

Figure 3:
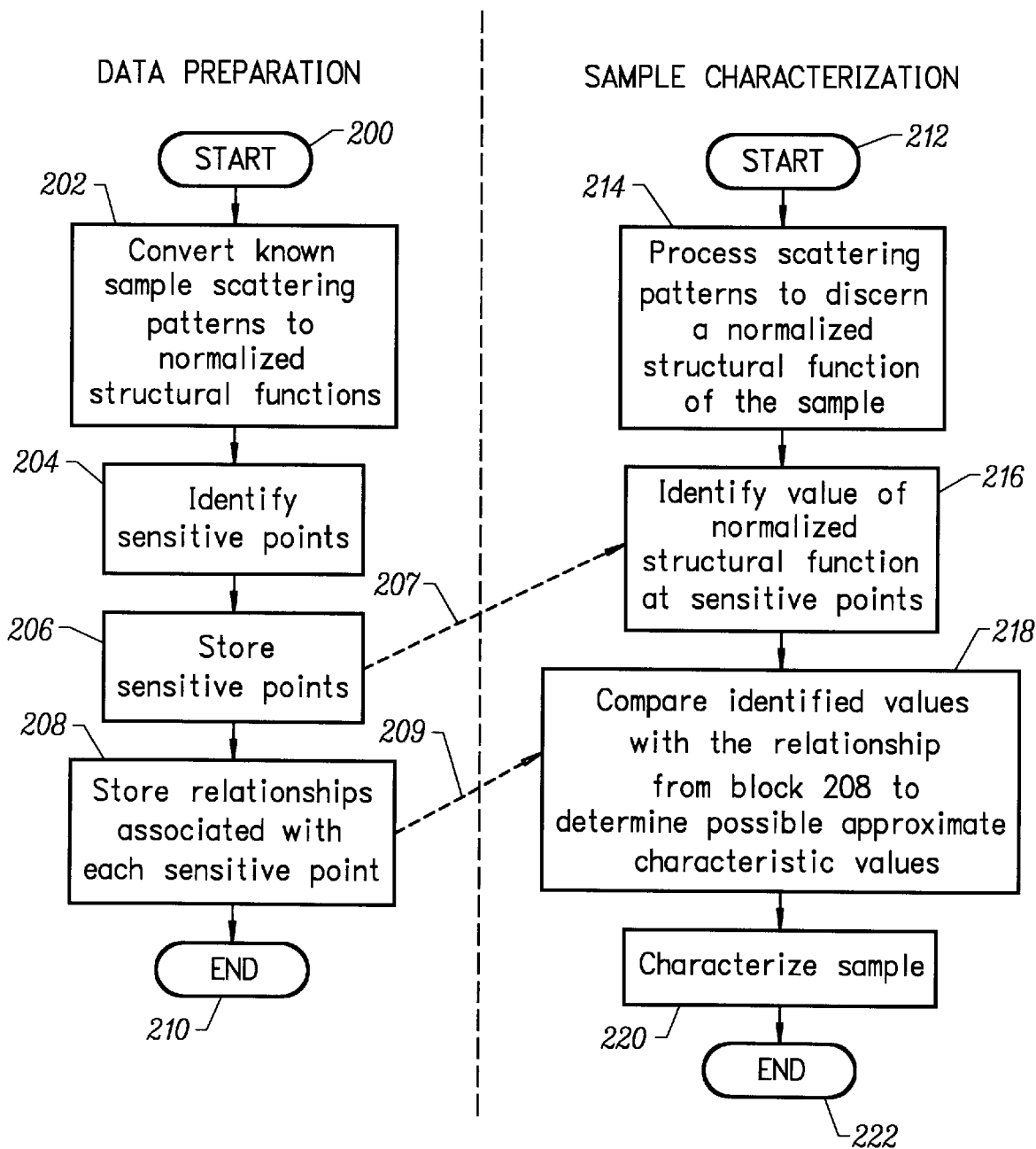
FIG. 3 is a generalized illustration of the methods according to the present invention.

FIG. 3 provides an outline of the methods of the present invention. As illustrated, the methods can be divided into a data preparation phase and a sample characterization phase.

The methods and techniques associated with the data preparation phase will be described first. The data preparation starts at block 200 where a structural function associated with each known sample is accessed from the database. At block 202, each structural function is converted to a normalized structural function which is desired for use in the data preparation phase unless the desired structural function has previously been stored in the database.

To obtain the desired structural function, previously stored scattering patterns can be converted to PDDFs and vice versa. As described above, the scattering pattern and PDDF are related to one another by a Fourier transform as illustrated in Equations 1 and 2. Accordingly, Equations 1 and 2 can be used to convert back and forth between a scattering $$p(r) = \frac{1}{2\pi^2} \int_0^\infty I(h) hr \sin(hr) \, dh \quad (1)$$

$$I(h) = 4\pi \int_0^\infty p(r) \frac{\sin(hr)}{hr} \, dr \quad (2)$$

pattern and a PDDF or between a normalized scattering pattern and an NPDDF. In Equations 1 and 2, $h=(4\pi/\lambda)\sin\theta$ where $2\theta$ is the scattering angle, $\lambda$ is the x-ray wavelength, $I(h)$ represents the intensity of the radiation scattered at $2\theta$, r is the distance and $p(r)$ represents the value of the PDDF at distance r. These equations can also be re-written as summations when the data is stored as illustrated in FIG. 7.

The limits of integration in Equations 1 and 2 are zero and infinity, however, the scattering patterns which are determined for the present invention are over an interval extending from a to b. At small angles, the scattering pattern decays quickly over small intervals. As a result, the interval can be chosen such that the decay in the scattering pattern from a to b is so large that the integral over the integral from a to b is an acceptable substitute for the integral from zero to infinity.

A preferred technique for normalization begins with the PDDF. The Applicant has noted that the PDDF for biological examples consistently shows peaks at a particular distance. The existence of this peak provides a common reference to the PDDF for each sample 14. Accordingly, the NPDDF for each sample 14 can be determined by dividing the PDDF of each sample 14 by the value of the PDDF at the common reference. Suitable common references are typically found in the range from approximately 20–56 angstroms.

The value of the common reference may be different for different equipment and optical systems. As a result, the reference should be determined as a part of the equipment set-up. The applicants have found the existence of a reference at approximately 28 Angstroms. Once the NPDDF has been determined, a normalized scattering pattern can be determined by applying Equation 2 to the NPDDF.

Another preferred technique for normalization is to use the standard scattering pattern developed using an apparatus similar to the one illustrated in FIG. 2. As described above, the scattering pattern for the sample can be divided by the standard scattering pattern to yield a normalized scattering pattern. This normalized scattering pattern can be converted to an NPDDF using equations 1 and 2. Additionally the standard and sample scattering patterns can both be converted to PDDFs and then the PDDF for the sample can be divided by the PDDF for the standard to develop an NPDDF.

At block 204, the sensitive points are determined. As described, sensitive points are points along the structural function where the value of the normalized structural function is sensitive to changes in a particular characteristic such as the collagen concentration. For instance, when the normalized structural function is the NPDDF and the characteristic of interest is the collagen concentration, the sensitive points are the distances on the NPDDF where the value of the NPDDF illustrates the largest increases in response to increases in the collagen concentration. Similarly, when the normalized structural function is the normalized scattering pattern and the characteristic of interest is the adipose concentration, the sensitive points are the distances on the normalized scattering pattern where the value of the normalized scattering pattern illustrates the largest increases in response to increases in the adipose concentration.

The sensitive points can be determined using techniques for determining the level of correlation between two variables, specifically, the value of the characteristic of interest and the value of the normalized structural function at a particular point along the structural function. The points associated with the largest degree of correlation between the value characteristic and the structural function and the characteristic are selected as the sensitive points for that characteristic.

In identifying the sensitive points, the level of correlation is determined for a plurality of points along the structural function. The number of points is preferably each point along the structural function which is or can be associated with an associated structural function value but can also be a set of points among the points which are or can be associated with a structural function value.

The preferred method for determining the sensitive points stems from determining a relationship between the value of the characteristic of interest and the value of the structural function at a particular point along the structural function. The relationship can be expressed in a table such as a table correlating a particular value of the characteristic with a range of structural function values. The relationship can also be a mathematical function expressing the value of the characteristic as a function of the value of the structural function at a particular point.

A mathematical relationship can be determined by plotting the value of the characteristic for each of the known samples against the value of each known sample's structural function at a particular point. The relationship is determined by fitting a curve to the data in the plot. The curves which are fit to the data are preferably monotonic curves and most preferably a monotonic piecewise step function such as the function. Many curve fitting techniques are suitable, however, performing a least squares fit to a piecewise step function is the most preferred.

Figure 4:
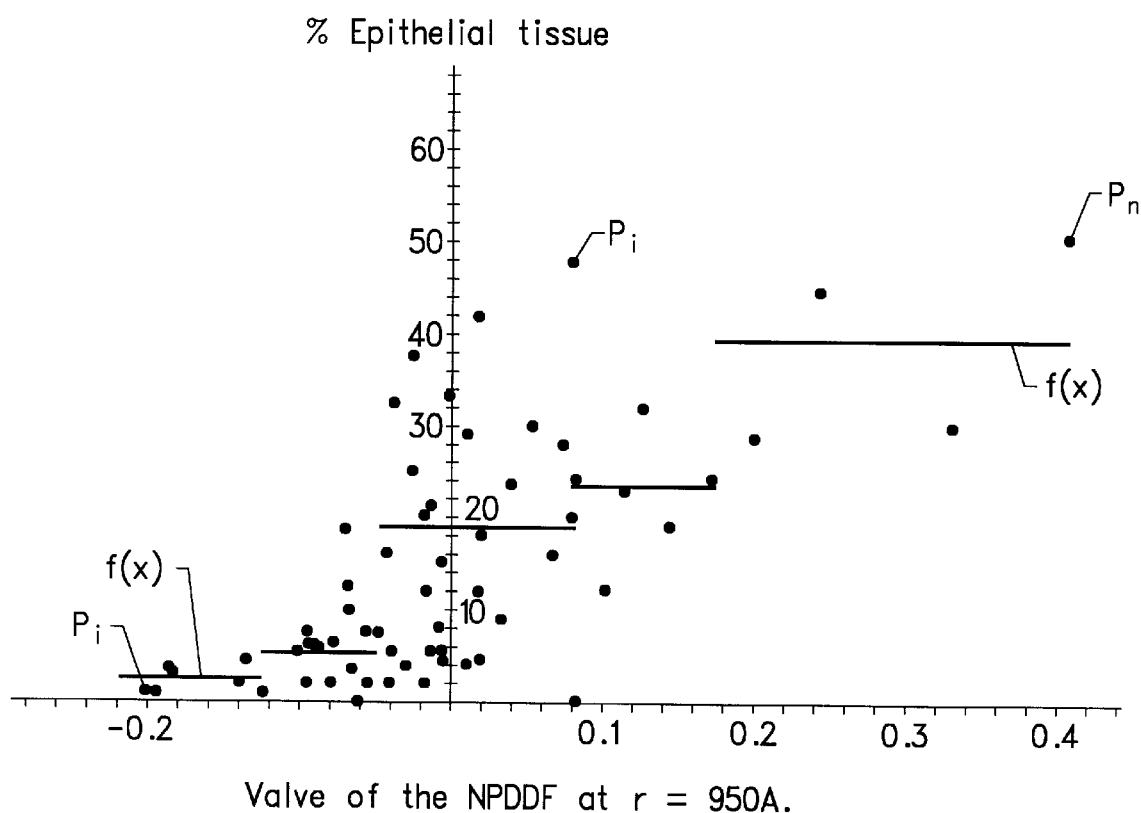
FIG. 4 illustrates a plot of the concentration of collagen in known samples versus the value of the normalized pair distance distribution function at a particular distance.

FIG. 4 illustrates a particular embodiment of the above method for determining a relationship expressed as a mathematical function. In FIG. 4, the % epithelial for each of the known samples, $p_i$, is plotted against the value of each known sample's NPDDF at approximately 950 Angstroms. The relationship is determined by fitting a curve to the data in the plot. The curve, $f(x)$, illustrated in FIG. 4 is a monotonic function and is more specifically a monotonic piecewise step function.

As described above, the relationships can also be expressed in tabular form. An example of a table is a table which associates a particular characteristic value with a range of values of the normalized structural function at a particular point on the normalized structural function. Such a table can be determined by identifying known samples which have a normalized structural function value at a particular point along their normalized structural function falling within a particular range to be specified in the table. The values of the characteristic associated with the identified known samples are then averaged and the averaged value is associated with the range specified in the table. This technique is repeated for each range to be specified in the table.

The values of the structural function used to determine the relationships as described above are taken at a particular point along the structural function, accordingly, each relationship is associated with a particular point along the structural function.

$$\text{Mean Deviation} = \sqrt{\frac{1}{n}\sum_{i=1}^{n}(p_i - f(x_i))^2} \qquad (3)$$

$$\text{Variaton} = \frac{f(x_n) - f(x_1)}{x_n - x_1} \qquad (4)$$

Once each relationship has been determined, the mean deviation of each relationship is also determined. The mean deviation can be determined using equation 3 where n is the number of characteristic values used to develop the relationship, $p_i$ is the characteristic value of the ith point used to create the relationship, $x_i$ is the value of the normalized structural function at a particular point, $f(x_i)$ is the value of the characteristic as indicated by the relationship at $x_i$. Since each relationship is associated with a point along the structural function, the mean deviations of each relationship can be plotted against the points along the structural function as illustrated in curve 1 of FIG. 5.

Figure 5:
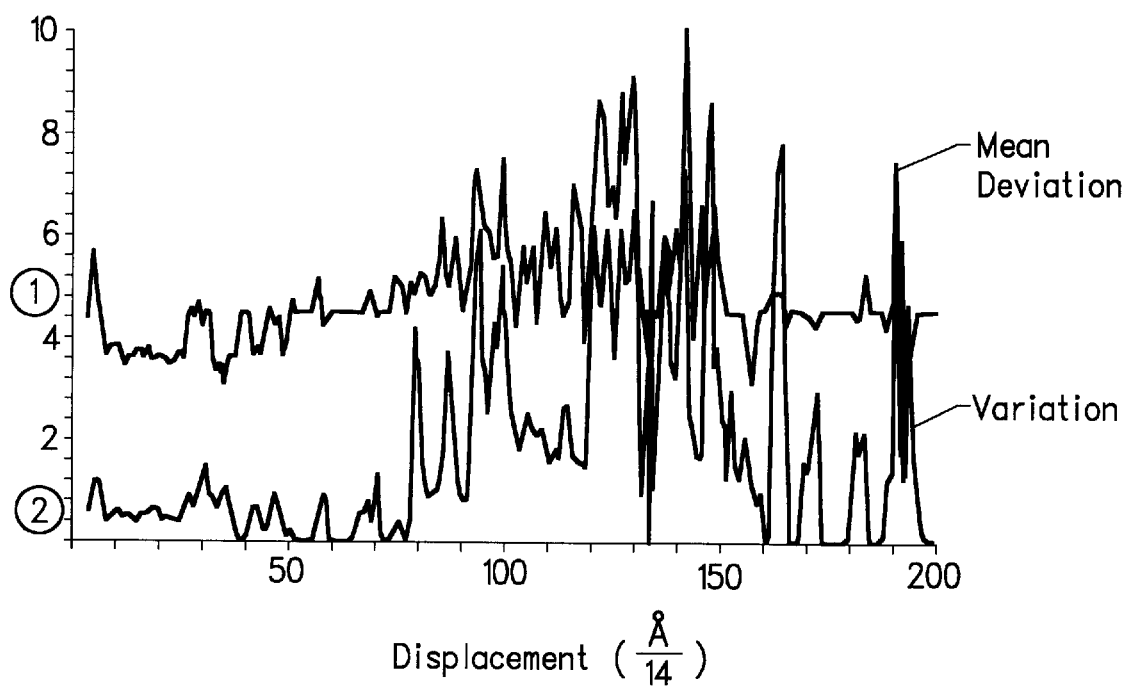
FIG. 5 graphically illustrates a technique for identifying points in the normalized structural function which are sensitive to changes in a particular characteristic.

Similarly, the variation in each relationship can also be determined and plotted against the points along the structural function as illustrated in curve 2 of FIG. 5. The variation for each relationship can be determined via Equation 4. The points on FIG. 5 where a minimum in the mean deviation are correlated with a maximum in the variation are selected as the sensitive points. For instance, the point at approximately 135 in FIG. 5 is a sensitive point. It is noted that FIG. 5 is provided for illustrative purposes only and that the described procedure for identifying the sensitive points can be performed without physically creating a plot such as the plot shown in FIG. 5. This preferred technique for identifying the sensitive points takes into consideration not only the quality of fit between the data and the determined relationship but also the degree of sensitivity indicated by the relationship.

At block 206 of FIG. 3, the identified sensitive points are stored for later use in the sample characterization phase as is illustrated by the arrow 207. Similarly, at block 208, the relationships which are associated with each identified sensitive point are stored for later use as illustrated by the arrow 209 in FIG. 3. Since the data for a particular characteristic is used in the creation of the relationships described above, each identified sensitive point and its associated relationship is associated with the particular characteristic. However, the data preparation phase can be repeated using a different characteristics to yield sensitive points and associated relationships associated with a different characteristic. Further, the normalized structural functions which are used in the creation of each relationship are all associated with the same class of known samples, accordingly, each sensitive point is also associated with a particular class of sample in addition to being associated with a particular characteristic. The data preparation phase terminates at end block 210.

FIG. 3 also illustrates a generalized version of the sample characterization phase. The sample characterization phase is based on quantifying a particular characteristic of the sample. A user can choose the characteristic to be quantified or a system can be programmed to work from a single characteristic or characteristics. As discussed above, the data preparation phase produces data which is associated with a particular characteristic. At least a portion of the data from the data preparation phase must be associated with the characteristic to be quantified in the sample preparation phase.

The sample characterization phase is started at block 212 when the user notifies the system that a sample 14 has been positioned in the apparatus 10. At block 214, the scattering pattern of the sample 14 is determined via operation of the apparatus 10. The determined scattering pattern is processed to determine a normalized structural function for the sample 14. At block 216, the value of the normalized structural function is identified at the sensitive points stored during the data preparation phase.

At block 218, the identified normalized structural function values are compared against the relationships stored during the data preparation phase. Specifically, each identified value is compared to the relationship which is associated with the same sensitive point as the identified value. For instance, when the relationships express the characteristic as a mathematical function of the value of the structural function, each identified value of the normalized structural function is substituted into a relationship which is associated with the same sensitive point as the sensitive point where the value was identified. Each substitution yields a possible approximate value for the characteristic.

When the relationship is expressed in a tabular form, each identified value of the normalized structural function is compared with a table which is associated with the same sensitive point as the identified value. Suitable tabular forms include, but are not limited to, a table correlating a particular value of the characteristic with a range of structural function values. During the comparison, each identified structural function value is determined to fall within a range specified in its associated table. The value of the characteristic associated with the identified range is the possible approximate characteristic value.

Whether the relationship is expressed as a function or a table, each relationship is associated with a particular sensitive point. Accordingly, the above comparisons result in a possible approximate value associated with each sensitive point. As described above, each sensitive point is associated with a class and a characteristic, accordingly, each possible approximate characteristic value is associated with a class and a characteristic. The possible approximate characteristic values which are associated with the characteristic of interest are selected.

At block 220, the sample is characterized. The selected possible approximate characteristic values associated with a different classes are averaged and their deviation determined. The sample 14 is then characterized as belonging to the class with the lowest deviation. Since suitable classifications include benign, normal and malignant, the cancer status of the sample can be determined by the above methods. The sample 14 is also characterized as having a characteristic value equal to the average of the possible approximate characteristic values associated with the selected class. When the known samples in the database are not classified, the sample 14 is merely characterized as having a characteristic value equal to the average of the possible approximate characteristic values. Each of the above possible characteristic values, averages, deviations and classifications should be provided to the user on a characteristic report so the user is able determine the quality of the characterization. The sample characterization phase terminates at end block 222.

The methods discussed with respect to FIG. 3 can be carried out using normalized scattering patterns, NPDDFs or a combination of both, however, the NPDDF is the preferred structural function for carrying out both the data preparation phase and the sample characterization phase. Further, normalization of the structural functions is preferred but is optional. Accordingly, the methods can also be carried out using the un-normalized PDDF and scattering pattern.

Figure 6A:
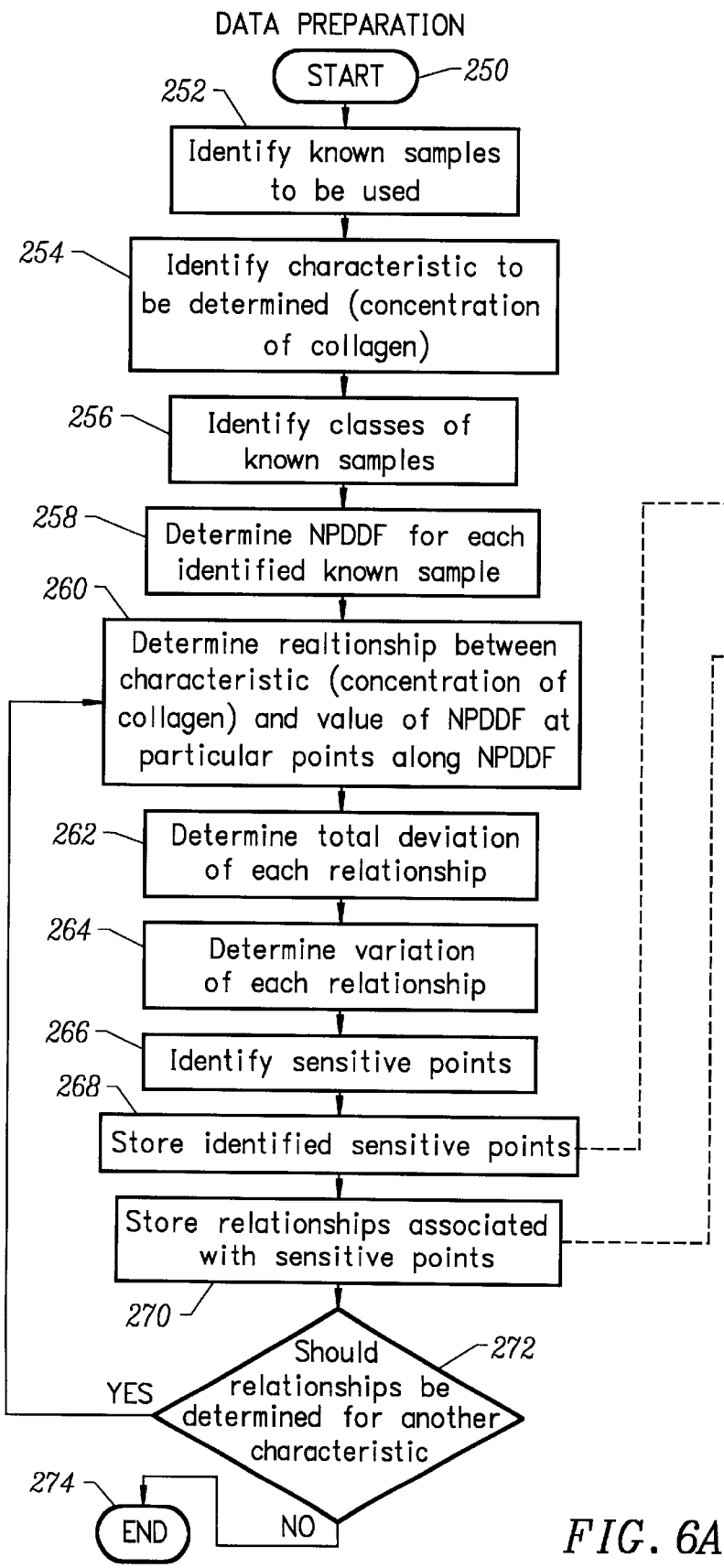
FIG. 6 illustrates an embodiment of a method according to the present invention.
Figure 6B:
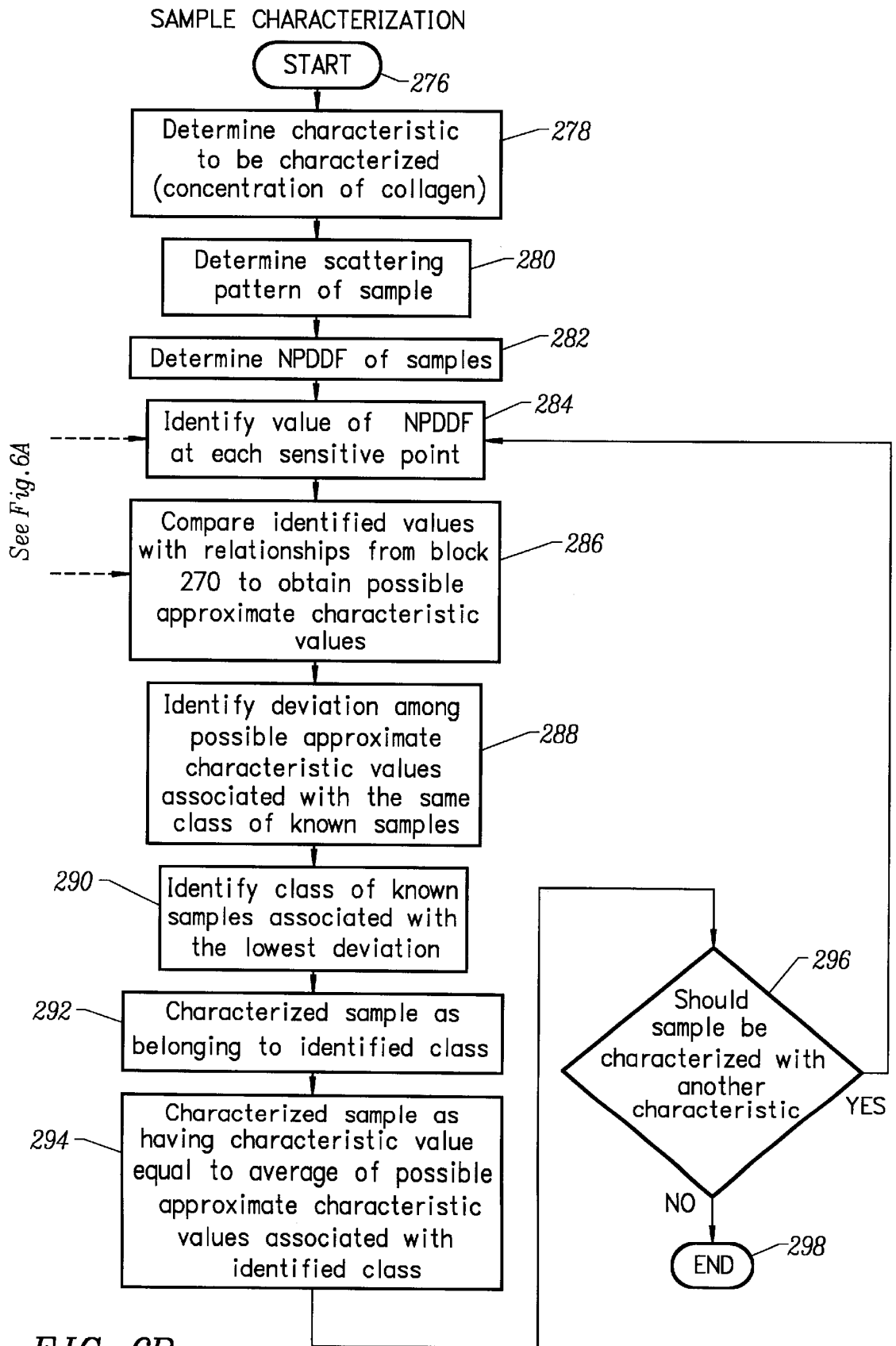

FIG. 6 provides a more detailed illustration of a method according to the present invention. The data preparation phase begins at block 250 when a user requests that data be prepared for use in the sample characterization phase. At block 252 the known samples which are to be used in the data preparation are determined. The determination can be made by providing a user with a list of the known samples and then requesting that the user select known samples from the list. The selection can take place with a user interface 40 such as a mouse or keyboard. This selection allows a user to exclude certain known samples from the data preparation. This may be desirable when certain known samples are known to have unusual characteristics.

At block 254, the characteristic to be determined is identified. The user can indicate one or more characteristics by selecting characteristics from a menu of characteristics. This selection process can be done via a typical user interface 40 such as a keyboard, mouse, etc.. When the goal of the sample characterization phase is cancer diagnosis, the preferred characteristic selection is the concentration of connective tissues such as collagen. Accordingly, collagen concentration will be presumed to be the selected characteristic for the remainder of the discussion with respect to FIG. 6.

At block 256, the classes into which the known samples are to be divided is determined. Again, the system can present the user with a menu of possible classifications and the user can use a typical user interface 40 to select the classes into which the known sample are divided. For the purpose of cancer diagnosis, the preferred classes are normal, benign and malignant. Accordingly, for the remainder of the discussion of FIG. 6, normal, malignant and benign will be presumed to be the selected classes.

At block 258, the NPDDF for each known sample identified at block 252 is determined. This determination can be done by using the techniques discussed above with respect to block 202 in FIG. 3 or the NPDDF for each known sample can be determined at some previous time and stored in the memory 34.

At block 260, relationships between the concentration of the collagen in the known samples and the associated value of the NPDDF are determined. The relationship can be determined from a plot of the collagen concentration for the known samples versus the value of the NPDDF at a particular distance such as the plot illustrated in FIG. 4. The value of the collagen concentration which is associated with each NPDDF value on the plot is the collagen concentration associated with the same known sample as the NPDDF value. Once the plot is created, the relationship is determined by performing a least squares fit of a monotonic piecewise step function to the plotted data.

A relationship is determined for a plurality point along the NPDDF value over a range of the NPDDF. This range is limited by the interval of the initial scattering pattern determined for the known samples. Accordingly, each relationship is associated with a particular point along the NPDDF. Further, the known samples which are used to create each relationship are drawn from the same class. Accordingly, each relationship is also associated with a particular class of known samples.

At block 262 the mean deviation of each relationship is determined. The mean deviation is determined by summing up the deviation of each point in each plot from the determined relationship. At block 264 the total variation of each plot is determined by application of Equation 5 to each plot.

At block 266 the sensitive points are selected. The sensitive points are selected by plotting the variation and the mean deviation versus each point along the NPDDF as is illustrated in FIG. 5. The points on the plot where a minimum in the deviation are matched with a maximum in the variation are chosen as the sensitive points. Each of these plots is created using the data associated with a particular class of known samples. Accordingly, each sensitive point is associated with a class of known samples.

At block 268 the identified sensitive points are stored for use in the sample characterization phase. At block 270, the relationship associated with each identified sensitive point is also stored for use in the sample characterization phase. The stored relationships are each associated with a particular sensitive point, with a particular characteristic and with a particular class of known samples.

At block 272, a determination is made whether the sensitive points and relationships are to be determined for another characteristic. The determination is positive if data associated with each characteristic identified in block 254 has not yet been prepared and stored. When the determination is positive, the system returns to block 260. When the determination is negative, the data preparation phase stops at block 274.

The sample characterization phase begins at block 276 when the user notifies the system that a sample 14 has been placed in the sample receiving volume 12. The notification can take place with a user interface 40 such as a mouse or a keyboard. At block 278, the one or more characteristics which the user wishes to be characterized are identified. When using the method for cancer diagnosis, the preferred characteristic is collagen concentration so the following discussion presumes that collagen concentration has been selected. Again, a user interface 40 such as a mouse or keyboard can be used to select the characteristic from a menu. At block 280 the processing unit 32 determines the scattering pattern of the sample 14 by activating the radiation source 16 and processing signals from the detector 28.

At block 282, the processing unit 32 processes the determined scattering pattern for the sample 14 to determine the NPDDF of the sample 14. At block 284, the value of the NPDDF at each sensitive point is identified. At block 286, each identified NPDDF value is compared with a relationship from the data preparation phase. Each identified NPDDF value is compared to a relationship which is associated with the same class, sensitive point and characteristics as the identified NPDDF value.

Since the relationships are expressed as piecewise step functions, a range of NPDDF values is associated with a particular value of the collagen concentrations in the sample 14. Comparing an identified NPDDF value with a relationship includes determining which range of NPDDF values the identified NPDDF value falls within. The collagen concentration associated with the determined range is the possible approximate value of the collagen concentration in the sample 14. Accordingly, comparing each identified NPDDF value with a relationship which is associated with a sensitive point and a class of known samples results in the determination of possible approximate values of the collagen concentration which are each associated with a sensitive point and a class of known samples.

$$\text{Coefficient of variation} = \frac{\text{Standard Deviation}}{\text{Mean Possible Approximate Values}} \quad (5)$$

At block 288, the coefficient deviation among the possible approximate values of the collagen concentration is determined for values which are associated with the same class. Alternatively, the coefficient of variation can be determined according to Equation 5 where the mean possible approximate values is the mean for the possible approximate values which are associated with the same class. At block 290, the sample 14 is characterized by identifying the class associated with the lowest deviation or with the lowest coefficient of variation. At block 292, the sample 14 is characterized as belonging to the class of known samples associated with the lowest deviation. For instance, if the class with the lowest deviation is fibroadenoma, the sample is characterized as including fibroadenoma. At block 294, the sample 14 is also characterized as having a concentration of collagen which is equal to the mean possible approximate values which are associated with the identified class.

At block 296, a determination is made whether the sample 14 should be characterized using another characteristic. For instance, should the characterization be repeated using the adipose concentration. The determination can be made by identifying whether each characteristic selected by the user at block 278 has been used to characterize the sample 14. When the determination is negative the system returns to block 284 and when the determination is positive the system proceeds to block 298.

At block 298, the user is provided with a characterization report 36. The report 36 summarizes the result of the above characterization. Specifically, the report 36 can provide the averages, deviations and classifications described above. The user can then examine the report 36 to determine the accuracy of the characterization. For instance, the deviation associated with the characterized class may be too high for the characterization to be accurate. Further, the deviation may be only slightly smaller than the deviation associated with another class which would bring the characterization into question. These factors can also be considered by the processing unit 32 which can indicate to the user the statistical quality of the characterization. After the characterization report 36 is provided to the user the sample characterization phase ends at block 298.

It is understood that blocks 252, and 254, 256 and 278 of FIG. 6 are optional. For instance, the system may work from a single characteristic such as the concentration of collagen and may automatically have the known samples divided into classes. Further, the system may not use classes at all and may simply characterize the sample 14 as having the average of the possible approximate values.

It is also understood that the sensitive points need not be identified to practice the methods of the present invention. Each point along the structural function which is or can be associated with a value of the structural function can be considered a sensitive point and the methods can proceed accordingly.

The above descriptions are intended to be illustrative only. For instance, once the normalized structural functions are determined for each known sample, the scattering patterns for the associated known sample can be replaced with the normalized structural function and the data preparation phase can begin at block 258 of FIG. 6. Additionally, once the sensitive points are positively identified, the relationships associated with each sensitive point can be determined without having to determine relationships for each point along the normalized structural function. Accordingly, additional known samples can be added to the database and the new relationships can be determined without re-identifying the sensitive points. Further, once the results of the data preparation phase are definitively determined, the sample characterization phase can be practiced without ever practicing the data preparation phase. Specifically, once the sensitive points have been identified and the relationships between a characteristic and the value of the normalized structural function at the sensitive points has been determined, many different users can use this data to perform the sample characterization phase for the characteristic without ever performing the data preparation phase. As a result, it is possible for the sample characterization phase to exist independently of the data preparation phase.

Many of the above methods are described as being performed from a plot of various data sets. These plots are provided for illustrative purposes only and the plots do not need to be created to practice the present invention. For instance, the process of fitting a curve to data points without actually plotting the data is well known. Similarly, matching minimums in deviation values with maximums in variation values can be performed without actually plotting the deviation and variation values.

The logic for performing the above methods can be included in any machine readable form such a CD, floppy disk, hard drive or hand held computer. Similarly, the logic can be located remote from the processing unit 32 such as on a network. Further, it is understood that much of the above methods can be carried out by hand. For instance, provided with the scattering pattern for a sample, the sensitive points in the scattering pattern and the relationships expressing a characteristic as a function of the value of the scattering pattern at the sensitive points, a user can manually identify the value of the scattering pattern at the sensitive points and compare the identified values with the relationships to determine possible and approximate values of the characteristic. Accordingly, a processing unit 32 is not needed to perform some methods or some portion of the methods of the present invention.

While the present invention is disclosed by reference to the preferred embodiments and examples detailed above, it is to be understood that these examples are intended in an illustrative rather than limiting sense, as it is contemplated that modifications and combinations will readily occur to those skilled in the art, which modifications and combinations will be within the spirit of the invention and the scope of the appended claims. For instance, the above methods can be performed without normalizing the structural functions. Additionally, when the sample characterization phase uses the scattering pattern but does not use the PDDF, the sample characterization phase can be carried out using value of the scattering pattern at a few discrete points. As a result, many of the above methods can be carried out using segments or discrete points of a structural function and a continuous structural function is not always required. Further, the above methods are not limited to biological samples and can be applied to nearly any material, preferably materials with periodic structures or materials which show diffraction capabilities.

What is claimed is:

1. A method for analyzing a characteristic of a test sample of biological tissue, comprising:

obtaining a radiation scattering pattern produced by the test sample of biological tissue;

processing the radiation scattering pattern to determine a pair distance distribution function for the test sample; and comparing the test sample pair distance distribution function with pair distance distribution functions of control samples of biological tissue which each have a known property with regard to the characteristic being analyzed the comparison being performed where the control pair distance distribution functions are sensitive to change in relation to the characteristic being analyzed.

2. The method of claim 1, further comprising:

normalizing the test sample pair distance distribution function after processing the radiation scattering pattern.

3. The method of claim 1, wherein the characteristic to be analyzed is selected from the group consisting of collagen concentration, fat concentration and epithelial concentration.

4. The method of claim 1, wherein the characteristic to be analyzed is whether the test sample of biological tissue comprises normal, benign or malignant tissue.

5. The method of claim 1, wherein processing the radiation scattering pattern includes performing a Fourier transform on the radiation scattering pattern to determine the pair distance distribution function of the test sample, identifying a value of the pair distance distribution function at a pre-determined pair distance, and dividing at least a portion of the pair distance distribution function by the identified value of the pair distance distribution function in order to normalize the pair distance distribution function.

6. The method of claim 5, wherein the predetermined pair distance is the pair distance where a pair distance distribution function for each of the control samples exhibits a peak.

7. The method of claim 5, wherein the identified pair distance is about 28 Angstroms.

8. The method of claim 1, further comprising:

processing the test sample pair distance distribution function to determine a normalized scattering pattern for the test sample.

9. The method of claim 8, wherein the comparison is performed at a particular angle where the function is sensitive to change in relation to the characteristic being analyzed.

10. The method of claim 1, wherein comparing the test sample pair distance distribution function with the pair distance distribution functions of the control samples includes creating a mathematical function between the functions.

11. The method of claim 10, wherein the characteristic to be analyzed is selected from the group consisting of the concentration of collagen, the concentration of fat and the concentration of epithelial.

12. The method of claim 10, wherein the mathematical function is a piecewise step-function.

13. The method of claim 1, wherein the test sample is an in vivo sample.

14. The method of claim 1, wherein the test sample is in its natural state.

15. A method for characterizing a test sample of biological tissue, comprising:

obtaining a radiation scattering pattern produced by the test sample of biological tissue;

processing the radiation scattering pattern to determine a pair distance distribution function for the test sample; and comparing sample data derived from the pair distance distribution function with known data derived from known samples which each have one or more known characteristics;

wherein the known data is a relationship between the value of the characteristic and a value of the pair distance distribution function at a particular pair distance.

16. The method of claim 15, wherein the value of the characteristic is selected from the group consisting of the concentration of collagen, the concentration of collagen and the concentration of epithelial.

17. The method of claim 15, wherein the relationship is expressed as a mathematical function.

18. The method of claim 17, wherein the mathematical function is a piecewise step-function.

19. A method for characterizing a test sample of biological tissue, comprising:

obtaining a radiation scattering pattern produced by the test sample of biological tissue;

processing the radiation scattering pattern to determine a pair distance distribution function for the test sample; and comparing sample data derived from the pair distance distribution function with known data derived from known samples which each have one or more known characteristics, wherein the known data is subdivided into known data sets, each known data set being associated with a particular class of known sample, and wherein comparing the sample data comprising identifying a value of the pair distance distribution function at one or more sensitive pair distances where a value of the pair distance distribution function is sensitive to changes in the value of the characteristic, each sensitive pair distance being associated with a particular class of known sample;

providing a mathematical relationships between the value of the characteristic and the value of the pair distance distribution function at each of the one or more sensitive pair distances, substituting each identified value into the mathematical relationship associated with the same sensitive pair distance as the identified value, the substitutions yielding a plurality of potential approximate characteristic values which are each associated with a class of known samples, finding the deviation among the potential approximate characteristic values associated with a particular class of known samples for each class of known samples, identifying the class of known samples associated with the lowest deviation; and characterizing the test sample as belonging to the identified class.

20. The method of claim 19, further comprising:

determining the average of the potential approximate characteristic values associated with the identified class; and characterizing the value of the characteristic of the test sample as being approximately the determined average.

21. A computer readable medium which has stored thereon computer executable logic which, when executed by a processor, causes processor to perform the acts of:

processing data regarding a radiation scattering pattern obtained from a test sample of biological material to determine a pair distance distribution function for the test sample; and comparing the test sample pair distance distribution function with pair distance distribution functions of control samples of biological tissue which each have a known property with regard to the characteristic being analyzed, the comparison being performed where the control pair distance distribution functions are sensitive to change in relation to the characteristic being analyzed.

22. The medium of claim 21, further comprising:

normalizing the test sample pair distance distribution function after processing the radiation scattering pattern.

23. The medium of claim 21, wherein processing the radiation scattering pattern includes:

performing a Fourier transform on the radiation scattering pattern to determine a pair distance distribution function of the test sample, identifying a value of the pair distance distribution function at a pre-determined pair distance, and dividing at least a portion of the pair distance distribution function by the identified value of the pair distance distribution function in order to obtain the pair distance distribution function.

24. The medium of claim 23, wherein the predetermined pair distance is the pair distance where a pair distance distribution function for each of the known samples exhibits a peak.

25. The medium of claim 21, further comprising:

processing the test sample pair distance distribution function to determine a normalized scattering pattern for the test sample.

26. The medium of claim 21, wherein the characteristic to be analyzed is whether the test sample of biological tissue comprises normal, benign or malignant tissue.

27. A computer readable medium which has stored thereon computer executable logic which, when executed bv a processor, causes the processor to perform the acts of:

processing data regarding a radiation scattering pattern obtained from a test sample of biological material to determine a pair distance distribution function for the test sample; and comparing the test sample pair distance distribution function with pair distance distribution functions of control samples of different classes of biological tissue, the comparisons being performed for each class where the control pair distance distribution function for that class is sensitive to chance in relation to that characteristic, determining the class to which the test sample belongs by identifying which class the test sample best matches based on the comparisons between the test sample pair distance distribution function and the control pair distance distribution functions for the different classes of biological tissue.

28. The medium of claim 27 wherein a best match is determined based on which control pair distance distribution function the test sample pair distance distribution function least deviates where the control pair distance distribution function for that class is sensitive to change.

* * * * *